(12) United States Patent
Oschmann

(10) Patent No.: US 6,399,099 B1
(45) Date of Patent: *Jun. 4, 2002

(54) EFFERVESCENT COMPOSITION WITH DRY EXTRACT OF GINKGO BILOBA

(75) Inventor: Rainer Oschmann, Landau (DE)

(73) Assignee: Dr. Willmar Schwabe GmbH & Co., Karlsruhe (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,896

(22) PCT Filed: Mar. 15, 1996

(86) PCT No.: PCT/EP96/01135

§ 371 (c)(1),
(2), (4) Date: Sep. 17, 1997

(87) PCT Pub. No.: WO96/29085

PCT Pub. Date: Sep. 26, 1996

(30) Foreign Application Priority Data

Mar. 17, 1995 (DE) .......................... 195 09 856

(51) Int. Cl.[7] .......................... A61K 9/46; A61K 35/78
(52) U.S. Cl. .................. 424/466; 424/195.1; 424/489; 514/772.3; 514/784
(58) Field of Search ............................ 424/466, 467, 424/489, 195.1, 465

(56) References Cited

U.S. PATENT DOCUMENTS 5,082,666 A * 1/1992 Rene et al. ................. 424/467

FOREIGN PATENT DOCUMENTS

| DE | 3723735 | * | 2/1988 |
| DE | 3832277 | * | 9/1988 |
| EP | 0 431 536 A1 | * | 6/1991 |

OTHER PUBLICATIONS

Dr. W. A. Ritschell, Die Tablette, Grundlagen and Praxis des Tablettierens, Granulierens and Dragierens, Edition Cantor KG/Aulendorf i. Wurtt, pp. 48 and 49, 108, 115, 117, 118, 119 and 137–142.
Rudof Voigt, Pharmazeutische Technologic, 7 uberarbeitete Auflage, Berlin, Ullstein Mosby (1993), pp. 238–239.
P. C. Schmidt and I. Christin, Brausetabletten–eine fast vergessene Arzneiform, Pharmazie 45(1990), H.2, pp. 89–101.
JP 07069862–A (cited in the ISR).
Bundesanzeiger No. 133, p. 7362, Jul. 19, 1994.

* cited by examiner

Primary Examiner—James M. Spear
(74) Attorney, Agent, or Firm—McDonnell Boehnen Hulbert & Berghoff

(57) ABSTRACT

The invention relates to effervescent compositions containing a dry extract of ginkgo biloba and an effervescent mixture. By dissolving the mixture in water a virtually clear and almost neutral solution is produced which is stable during the period of use.

25 Claims, No Drawings

EFFERVESCENT COMPOSITION WITH DRY EXTRACT OF GINKGO BILOBA

This application is a 371 of PCT/EP96/01135 filed Mar. 15, 1996.

It has been proved by a great number of clinical trials that the active agent of ginkgo biloba leaves, extracted with acetone-water is effective in a number of diseases in the field of peripheral and cerebral circulatory disturbances. These results have caused the commission E at the German Federal Health Office [Kommission E beim Deutschen Bundesgesundheitsamt] to pass a monography (Federal Gazette [Bundesanzeiger] No. 133 of Jul. 19, 1994) stating of the following indications:

for the symptomatic treatment of cerebro-organic induced vitality deficiencies in connection with a whole therapeutic concept in demential syndroms with the principle symptoms: dismnesia, lack of concentration, depressive mood, dizziness, susurrus aurium, headache;

improvement of the painfree walking range in peripheral, arterial occlusive disease at stage II according to Fontaine (Claudicatio intermittens) in connection with physical-therapeutical measures, particularly walking training;

dizziness, tinnitus (noise in the ears) of vascular and involutional origin.

The effect of the dry extracts of ginkgo biloba leaves may be caused by one therapeutically effective component or by a combination of many effective components. The most important therapeutically effective components are flavonoids, such as ginkgo flavone glycosides and terpenoids, e.g. ginkgolides and bilobalides. Accordingly pharmaceutical preparations are standardized on said components. One of these dry extracts, EGb 761, contains about 24% ginkgo flavone glycosides and about 6% terpenes; see Jos Kleijnen, Paul Knipschild, The Lancet Nov. 7, 1992, Vol. 340, 1136. Further dry extracts and processes for their preparation and their use are described in German patents DE 39 40 091 and DE 39 40 092.

The active agent is usually administered in the form of tablets or as a solution, in which nonaqueous solvents, such as ethanol or propylene glycol must be used. Purely aqueous solutions are not available because on the one hand certain components show a very poor solubility in water, like ginkgolides of less than 0.02%. On the other hand, some components, like bilobalide are not stable in neutral or slightly basic aqueous medium. Precipitations as well as chemical degradation processes of extract components occur in aqueous solutions. For these reasons it is not obvious to prepare effervescent preparations. Additionally the extract has hygroscopic, sticky characteristics which impair the processing to effervescent tablets.

However, there is a frequent need for purely aqueous preparations of a dry extract of ginkgo biloba leaves. Thus, the problem underlying the present invention is to provide a preparation of dry extracts of ginkgo biloba leaves in the form of an effervescent composition for which only water may be used as solvent for dissolving the effervescent composition, in which no notable degradation processes occur during the period of use, and which have a stability of the solution resulting after adding water of at least one hour.

This problem is solved by the development of an effervescent composition which comprises a ginkgo biloba dry extract and an effervescent mixture which contains a physiologically acceptable acid or sodium salt thereof and a physiologically acceptable carbonate or hydrogen carbonate in such a ratio that the resulting solution after adding water to the effervescent composition has a pH value of about 6 to 8 and is stable for at least one hour.

The weight ratio of acid to carbonate or hydrogen carbonate is preferably about 1:1 to 1:3.

By the addition of auxiliary agents and by determining the components of the effervescent mixture and thus of the conditions of the medium of the resulting solution after adding water a virtually clear solution can be obtained which is stable during the period of use. After dissolving the effervescent composition in water the resulting solution has a pH value of about 6 to 8.

The term "effervescent composition" when used herein means e.g. powder, granulate and tablets, preferably tablets.

Effervescent mixtures contain physiologically acceptable acids and carbonate or hydrogen carbonate for releasing $CO_2$. Specific examples for carbonates and hydrogen carbonates are sodium salts. These effervescent mixtures develop $CO_2$ along with their decomposition upon contact with water. To optimize the $CO_2$ development an excess of acid is usually added. This means for the resulting solutions slightly acidic pH values of 3 to 5. However, this medium is disadvantageous for the solution of the dry extracts of ginkgo biloba leaves. The use of a shortage of acid was surprisingly suitable for the preparation of the solutions according to this invention. Although the $CO_2$ development was reduced under these conditions, the resulting pH value of about 6 to 8 was suitable for dissolving the dry extracts.

By the addition of minor amounts of a physiologically acceptable water soluble surfactant the solubility of the dry extract is additionally positively influenced. Specific examples for preferred surfactants are polysorbates, i.e. non-ionic surfactants of the type of ethoxylated sorbitan esters, polyoxyethylene fatty acid esters, ethoxylated glycerol esters and sodium dioctylsulfosuccinate. The surfactant is preferably used in an amount of about 0.01 to 0.5% by weight, preferably 0.05% by weight.

An acceptable taste of the resulting solution of the dry extracts which have a bitter taste can be achieved by adding suitable taste improvement agents, e.g. flavouring agents, sugar or sugar surrogates. Sugar or sugar surrogates may be present in an amount of up to about 50% by weight. Suitable taste improvement agents for the preparation of the solutions according to this invention are artificial or natural sweetening agents, preferably saccharin-Na, sorbite, aspartame or mannite, preferably in an amount of about 0.5 to 5% by weight or artificial or natural flavouring agents, preferably lemon flavour or grapefruit flavour and mixtures thereof. The flavours are preferably used in an amount of about 0.5 to 3% weight, preferably 1% by weight.

The dosage of the dry extract per form of administration, e.g. tablet, is about 30 to 240 mg.

Suitable acids for the preparation of the effervescent compositions of the present invention are physiologically acceptable acids or mixtures thereof, preferably citric acid, monosodium citrate and tartaric acid, particularly citric acid and monosodium citrate.

Furthermore, water soluble auxiliary agents for tabletting are used, e.g. filling agents and binding agents, preferably mannite, lactose, sodium sulfate, polyvinylpyrrolidone or mixtures thereof and auxiliary agents, such as antifoaming emulsions, and lubricants, such as polyethylene glycols.

Example 1

Granulate consisting of:

| | |
|---|---|
| dry extract of *ginkgo biloba* leaves | 60 kg |
| citric acid | 160 kg |
| NaHCO$_3$ | 230 kg |
| mannite | 250 kg |
| PEG 20000 | 33 kg |
| saccharin-Na | 10 kg |
| lemon flavour | 7 kg |

Preparation

Dry extract, mannite and PEG 20000 are milled and sieved, and the remaining components are added. The mixture is compressed to tablets having a diameter of 13 mm and 800 mg. A virtually clear solution is obtained after dissolving within 3 minutes. The active agents are stable within one hour.

Example 2

Granulate consisting of:

| | |
|---|---|
| dry extract of *ginkgo biloba* leaves | 120 kg |
| citric acid | 320 kg |
| NaHCO$_3$ | 400 kg |
| Tween 80 | 0.6 kg |
| mannite | 660 kg |
| PEG 20000 | 65.4 kg |
| grapefruit flavour | 14 kg |
| saccharin-Na | 20 kg |

Preparation

Dry extract and PEG 20000 are mixed and a solution of Tween 80 (2% in ethanol) is added. The remaining components are added. The mixture is compressed to tablets having a diameter of 18 mm and 160 mg.

Example 3

A tablet produced according to example 1 or 2 is dissolved in 200 ml water producing a virtually clear solution. The solution is stable for at least one hour, i.e. the content of bilobalide is at least 90% of the starting value.

Example 4

Granulate consisting of:

| | |
|---|---|
| ginkgo extract | 80 kg |
| sodium hydrogen citrate | 450 kg |
| sodium carbonate | 200 kg |
| sodium hydrogen carbonate | 716 kg |
| sodium sulfate | 420 kg |
| lactose | 700 kg |
| Macrogol[1]-glycerol hydroxy stearate | 5 kg |
| Simethicon[2] antifoam emulsion | 15 kg |
| aspartame | 15 kg |
| lemon flavour | 55 kg |

[1]polyethylene glycols
[2]polydimethyl siloxane activated with silicon dioxide

[1] polyethylene glycols
[2] polydimethyl siloxane activated with silicon dioxide Preparation An active agent granulate is prepared from the extract, lactose, Macrogol glycerol hydroxy stearate and Simethicon by adding isopropanol and an effervescent mixture is produced from the citrates, sodium sulfate and sodium hydrogen carbonate. Both granulates are mixed, the remaining auxiliary agents are added and compressed to effervescent tablets of 80 mg.

What is claimed is:

1. An effervescent composition for oral administration comprising
    (a) a dry extract of ginkgo biloba comprising from 20–30% by weight of flavone glycosides and from about 4.5–8.5% by weight of terpenoids;
    (b) an effervescent mixture of a physiologically acceptable acid or sodium salt thereof; and
    (c) a physiologically acceptable carbonate or hydrogen carbonate in a weight ratio of (b) to (c) of about 1:1 to 1:3,
    where the resulting solution after adding water has a pH value of 6 to 8 and is stable for at least one hour.

2. An effervescent composition according to claim 1, wherein the acid is citric acid or tartaric acid or the monosodium salt thereof.

3. An effervescent composition according to claim 1, wherein the carbonate or hydrogen carbonate is the sodium salt.

4. An effervescent composition according to claim 1, further comprising of a physiologically acceptable water soluble surfactant.

5. An effervescent composition according to claim 4, wherein the surfactant is a polysorbate or sodium dioctylsulfosuccinate.

6. An effervescent composition according to claim 1, further comprising a sweetening agent.

7. An effervescent composition according to claim 1, further comprising a flavouring agent.

8. An effervescent composition according to claim 2, further comprising of a physiologically acceptable water soluble surfactant.

9. An effervescent composition according to claim 3, further comprising of a physiologically acceptable water soluble surfactant.

10. An effervescent composition according to claim 8, wherein the surfactant is a polysorbate or sodium dioctylsulfosuccinate.

11. An effervescent composition according to claim 2, further comprising a sweetening agent.

12. An effervescent composition according to claim 5, further comprising a sweetening agent.

13. An effervescent composition according to claim 2, further comprising a flavouring agent.

14. An effervescent composition according to claim 3, further comprising a flavouring agent.

15. An effervescent composition according to claim 4, further comprising a flavouring agent.

16. An effervescent composition according to claim 5, further comprising a flavouring agent.

17. An effervescent composition according to claim 6, further comprising a flavouring agent.

18. An effervescent composition according to claim 9, wherein the surfactant is a polysorbate or sodium dioctylsulfosuccinate.

19. An effervescent composition according to claim 4, further comprising a sweetening agent.

20. An effervescent composition according to claim 19, further comprising a flavoring agent.

21. An effervescent pharmaceutical composition for oral administration comprising
    (a) from 20–30% by weight flavone glycosides and from about 4.5–8.5% by weight of terpenoids;

(b) an effervescent mixture of a physiologically acceptable acid or sodium salt thereof; and (c) a physiologically acceptable carbonate or hydrogen carbonate in a weight ratio of (b) to (c) of about 1:1 to 1:3, where the resulting solution after adding water has a pH value of 6 to 8 and is stable for at least one hour.

22. An effervescent pharmaceutical composition for oral administration comprising (a) a dry extract of ginkgo biloba comprising from 22 to 26% by weight of flavone glycosides and from 4.5 to 8.5% by weight of terpenoids;

(b) an effervescent mixture of a physiologically acceptable acid or sodium salt thereof; and (c) a physiologically acceptable carbonate or hydrogen carbonate in a weight ratio of (b) to (c) of about 1:1 to 1:3, where the resulting solution after adding water has a pH value of 6 to 8 and is stable for at least one hour.

23. An effervescent pharmaceutical composition for oral administration comprising (a) a dry extract of ginkgo biloba comprising about 24% by weight of flavone glycosides and about 6% by weight of terpenoids;

(b) an effervescent mixture of a physiologically acceptable acid or sodium salt thereof; and (c) a physiologically acceptable carbonate or hydrogen carbonate in weight ratio of (b) to (c) of about 1:1 to 1:3, where the resulting solution after adding water has a pH value of 6 to 8 and is stable for at least one hour.

24. An effervescent pharmaceutical composition comprising (a) from 22 to 26% by weight flavone glycosides and from 4.5 to 8.5% by weight of terpenoids;

(b) an effervescent mixture of a physiologically acceptable acid or sodium salt thereof; and (c) a physiologically acceptable carbonate or hydrogen carbonate in a weight ration of (b) to (c) of about 1:1 to 1:3, where the resulting solution after adding water has a pH value of 6 to 8 and is stable for at least one hour.

25. An effervescent pharmaceutical composition comprising (a) about 24% by weight flavone glycosides and about 6% by weight of terpenoids;

(b) an effervescent mixture of a physiologically acceptable acid or sodium salt thereof; and (c) a physiologically acceptable carbonate or hydrogen carbonate in a weight ration of (b) to (c) of about 1:1 to 1:3, where the resulting solution after adding water has a pH value of 6 to 8 and is stable for at least one hour.

* * * * *